(12) United States Patent
Zhang et al.

(10) Patent No.: US 10,557,130 B2
(45) Date of Patent: Feb. 11, 2020

(54) ARGININE DEIMINASE MUTANT AND METHODS OF USING THE SAME

(71) Applicant: Jiangnan University, Wuxi (CN)

(72) Inventors: Tao Zhang, Wuxi (CN); Bo Jiang, Wuxi (CN); Hangyu Jiang, Wuxi (CN); Wanmeng Mu, Wuxi (CN); Ming Miao, Wuxi (CN)

(73) Assignee: Jiangnan University, Jiangsu, Wuxi (CN)

( * ) Notice: Subject to any disclaimer, the term of this patent is extended or adjusted under 35 U.S.C. 154(b) by 0 days.

(21) Appl. No.: 15/907,340

(22) Filed: Feb. 28, 2018

(65) Prior Publication Data

US 2018/0251748 A1    Sep. 6, 2018

(30) Foreign Application Priority Data

Mar. 2, 2017  (CN) .......................... 2017 1 0119423

(51) Int. Cl.
| | | |
|---|---|---|
| *C12N 9/96* | (2006.01) | |
| *C12N 9/78* | (2006.01) | |
| *C12P 13/10* | (2006.01) | |
| *A61P 35/02* | (2006.01) | |
| *C12N 15/70* | (2006.01) | |
| *A61K 38/50* | (2006.01) | |

(52) U.S. Cl.
CPC ................ *C12N 9/78* (2013.01); *A61K 38/50* (2013.01); *A61P 35/02* (2018.01); *C12N 15/70* (2013.01); *C12P 13/10* (2013.01); *C12Y 305/03006* (2013.01)

(58) Field of Classification Search
None
See application file for complete search history.

(56) References Cited

U.S. PATENT DOCUMENTS

| 6,737,259 B1 * | 5/2004 | Clark | ..................... A61K 38/50 |
| | | | 435/181 |
| 7,204,980 B2 * | 4/2007 | Clark | ..................... A61K 38/50 |
| | | | 424/94.1 |

* cited by examiner

*Primary Examiner* — Hope A Robinson
(74) *Attorney, Agent, or Firm* — IPro, PLLC; Na Xu

(57) ABSTRACT

An arginine deiminase mutant with improved enzyme activity and temperature stability and application thereof were provided, belonging to the technical field of genetic engineering and enzyme engineering. The arginine deiminase mutant is proline, namely Gly292 Pro, mutated from glycine near an enzyme active center. A wild-type arginine deiminase arcA coding gene is molecularly modified by a site-directed mutation technique to obtain a mutant enzyme ADIG292P, which has glycine at position 292 of an amino acid sequence of the wild type arginine deiminase mutated to proline. The arginine deiminase, modified by site-directed mutation, of the present invention has 1.5 times of increase in enzyme activity and 5.43 times of increase in half-life period at 40° C. compared with the wild-type enzyme, which solves the problems of low catalytic ability and temperature stability during the catalytic synthesis of citrulline using arginine deiminase, and lays a foundation for industrial production of efficient synthesis of citrulline and medication application.

6 Claims, 2 Drawing Sheets

Specification includes a Sequence Listing.

SEQUENCE LISTING

```
<160> NUMBER OF SEQ ID NOS: 6

<210> SEQ ID NO 1
<211> LENGTH: 408
<212> TYPE: PRT
<213> ORGANISM: Artificial Sequence
<220> FEATURE:
<223> OTHER INFORMATION: Protein translated from synthetic DNA

<400> SEQUENCE: 1

Met Ser His Pro Ile Asn Val Phe Ser Glu Ile Gly Lys Leu Lys Thr
1               5                   10                  15

Val Met Leu His Arg Pro Gly Lys Glu Leu Glu Asn Leu Met Pro Asp
            20                  25                  30

Tyr Leu Glu Arg Leu Leu Phe Asp Asp Ile Pro Phe Leu Glu Lys Ala
        35                  40                  45

Gln Ala Glu His Asp Ala Phe Ala Glu Leu Leu Arg Ser Lys Asp Ile
    50                  55                  60

Glu Val Val Tyr Leu Glu Asp Leu Ala Ala Glu Ala Leu Ile Asn Glu
65                  70                  75                  80
```

Glu Val Arg Arg Gln Phe Ile Asp Gln Phe Leu Glu Ala Asn Ile
            85                  90                  95

Arg Ser Glu Ser Ala Lys Glu Lys Val Arg Glu Leu Met Leu Glu Ile
        100                 105                 110

Asp Asp Asn Glu Glu Leu Ile Gln Lys Ala Ile Ala Gly Ile Gln Lys
            115                 120                 125

Gln Glu Leu Pro Lys Tyr Glu Gln Glu Phe Leu Thr Asp Met Val Glu
        130                 135                 140

Ala Asp Tyr Pro Phe Ile Ile Asp Pro Met Pro Asn Leu Tyr Phe Thr
145                 150                 155                 160

Arg Asp Asn Phe Ala Thr Met Gly His Gly Ile Ser Leu Asn His Met
                165                 170                 175

Tyr Ser Val Thr Arg Gln Arg Glu Thr Ile Phe Gly Gln Tyr Ile Phe
                180                 185                 190

Asp Tyr His Pro Arg Phe Ala Gly Lys Glu Val Pro Arg Val Tyr Asp
            195                 200                 205

Arg Ser Glu Ser Thr Arg Ile Glu Gly Gly Asp Glu Leu Ile Leu Ser
        210                 215                 220

Lys Glu Val Val Ala Ile Gly Ile Ser Gln Arg Thr Asp Ala Ala Ser
225                 230                 235                 240

Ile Glu Lys Ile Ala Arg Asn Ile Phe Glu Gln Lys Leu Gly Phe Lys
                245                 250                 255

Asn Ile Leu Ala Phe Asp Ile Gly Glu His Arg Lys Phe Met His Leu
                260                 265                 270

Asp Thr Val Phe Thr Met Ile Asp Tyr Asp Lys Phe Thr Ile His Pro
            275                 280                 285

Glu Ile Glu Pro Gly Leu Val Val Tyr Ser Ile Thr Glu Lys Ala Asp
        290                 295                 300

Gly Asp Ile Gln Ile Thr Lys Glu Lys Asp Thr Leu Asp Asn Ile Leu
305                 310                 315                 320

Cys Lys Tyr Leu His Leu Asp Asn Val Gln Leu Ile Arg Cys Gly Ala
                325                 330                 335

Gly Asn Leu Thr Ala Ala Ala Arg Glu Gln Trp Asn Asp Gly Ser Asn
                340                 345                 350

Thr Leu Ala Ile Ala Pro Gly Glu Val Val Val Tyr Asp Arg Asn Thr
            355                 360                 365

Ile Thr Asn Lys Ala Leu Glu Glu Ala Gly Val Lys Leu Asn Tyr Ile
        370                 375                 380

Pro Gly Ser Glu Leu Val Arg Gly Arg Gly Pro Arg Cys Met Ser
385                 390                 395                 400

Met Pro Leu Tyr Arg Glu Asp Leu
            405

<210> SEQ ID NO 2
<211> LENGTH: 1227
<212> TYPE: DNA
<213> ORGANISM: Artificial Sequence
<220> FEATURE:
<223> OTHER INFORMATION: Synthetic DNA

<400> SEQUENCE: 2
atgagtcatc caattaatgt attttctgaa atcggaaaat tgaaaacagt gatgttacat      60
cgtccaggta aggaattaga aaatttaatg ccagattatc tggagagact gttgtttgat     120
gatattccgt ttttagaaaa agcacaagca gaacatgatg catttgcaga gttgttacga     180

| | |
|---|---|
| tcaaaagata tcgaagtggt ctatttagag gacttagctg ctgaagcgtt gattaatgaa | 240 |
| gaggtccgcc gacaatttat tgaccaattc ttagaagaag ccaatattcg cagcgaatca | 300 |
| gcaaaagaaa aagttagaga gttaatgtta gaaattgacg acaacgaaga actgattcaa | 360 |
| aaagcgattg ctggcattca aaaacaagaa ttacctaaat atgagcaaga atttttaaca | 420 |
| gatatggttg aagcggatta tccattcatt attgatccaa tgcctaactt atacttcaca | 480 |
| cgtgataact ttgcgacaat gggccacggg atttctttaa atcatatgta ttcagtaact | 540 |
| cgacaacggg aaaccatttt tgggcaatac attttttgatt atcatcctcg ttttgctgga | 600 |
| aaagaggttc ctagagtcta tgatcgttca gaatcaacca gaattgaagg tggcgatgaa | 660 |
| ttaattcttt caaaagaagt ggtggccatt gggatttctc aaagaacgga cgccgcgtca | 720 |
| attgaaaaaa ttgcgagaaa tattttttgaa caaaaattag gattcaaaaa tatcttggct | 780 |
| tttgatatcg gtgaacatcg taaattcatg catttagata ccgttttttac catgattgac | 840 |
| tatgataaat ttacgattca tccagaaatc gaacctggct tggttgttta ctcgatcact | 900 |
| gaaaaagcag atggagacat ccaaattaca aagaaaaag atacattaga taacatttta | 960 |
| tgcaaatact tgcatttaga caatgttcaa ttaatccgtt gcggcgctgg aaatttaacc | 1020 |
| gcagcagccc gggaacaatg gaacgacggt tcaaatacat tagcaattgc ccctggggaa | 1080 |
| gttgttgttt acgatcggaa tacgattacg aataaagcgc tagaagaagc aggcgtgaaa | 1140 |
| ttgaattaca ttccaggaag tgaactagta cgtggccgtg gtggccctcg ttgtatgagt | 1200 |
| atgccacttt accgtgaaga tctttaa | 1227 |

```
<210> SEQ ID NO 3
<211> LENGTH: 29
<212> TYPE: DNA
<213> ORGANISM: Artificial Sequence
<220> FEATURE:
<223> OTHER INFORMATION: Synthetic DNA

<400> SEQUENCE: 3
cgcggatcca tgagtcatcc aattaatgt                                       29

<210> SEQ ID NO 4
<211> LENGTH: 26
<212> TYPE: DNA
<213> ORGANISM: artificial sequence
<220> FEATURE:
<223> OTHER INFORMATION: Synthetic DNA

<400> SEQUENCE: 4
ccgctcgagt taaagatctt cacggt                                          26

<210> SEQ ID NO 5
<211> LENGTH: 31
<212> TYPE: DNA
<213> ORGANISM: Artificial Sequence
<220> FEATURE:
<223> OTHER INFORMATION: Synthetic DNA

<400> SEQUENCE: 5
catccagaaa tcgaacctgg cttggttgtt t                                    31
```

```
<210> SEQ ID NO 6
<211> LENGTH: 33
<212> TYPE: DNA
<213> ORGANISM: Artificial Sequence
<220> FEATURE:
<223> OTHER INFORMATION: Synthetic DNA

<400> SEQUENCE: 6
ttcgatttct ggatgaatcg taaatttatc ata                              33
```

ARGININE DEIMINASE MUTANT AND METHODS OF USING THE SAME

CROSS REFERENCE TO RELATED APPLICATIONS

This application claims priority to Chinese Patent Application CN 201710119423.9 filed on Mar. 2, 2017, the entirety of the contents of which is incorporated herein by reference.

TECHNICAL FIELD

The disclosure herein relates to the field of genetic engineering and enzyme engineering, which relates to an arginine deiminase mutant with improved enzyme activity and temperature stability and application thereof.

BACKGROUND

Arginine deiminase (EC 3.5.3.6), abbreviated as ADI, can hydrolyze arginine to produce citrulline and ammonia. Since the first report in 1933, the enzyme has been found in *Streptococcus lactiae, Streptococcus faecalis*, yeast, pseudomonas, mycoplasma, halobacterium and some eukaryotic cells, etc. Arginine deaminase is wide in source, and has been found in bacteria, archaebacteria and some eukaryotic cells. There are obvious differences in properties of ADI of different microbial sources, such as molecular weight range, optimal pH, optimal temperature, etc. However, all the ADI has the ability to decompose arginine.

Citrulline, also called as carbamylornithine ornithin, gets the name as being extracted from watermelon initially. In recent years, it has been found by researches that citrulline has the physiological functions of scavenging free radicals, affecting nitrogen balance in the human body, immune regulation of the cardiovascular system, and the like. Therefore, the application of citrulline in food and medicine aspects is increasing. Because of the functions of aging resisting, immunity enhancement, athlete muscle strength and endurance improvement and the like of citrulline, citrulline has been added into sports functional drinks produced by a Canadian company. At the same time, health skin care products containing citrulline are also sold on the market in European and American countries.

Citrulline is mainly produced by four methods, i.e., a chemical method, an extraction method, a fermentation method and an enzymic method. Among them, the chemical method is currently the main production mode, but by-products such as copper ions and hydrogen sulfide produced during a production process have an adverse impact on the environment. Both the extraction method and the fermentation method for citrulline production have the of low yield and high cost, and thus are not conducive to large-scale production. On the contrary, the enzymatic method for citrulline production has the advantages of mild reaction conditions, high conversion efficiency, simple extraction process and the like, so the enzymatic method has high research and production value. Therefore, the search for safe and stable arginine deiminase with high catalytic efficiency is the key issue for enzymatic citrulline production.

Site-directed mutagenesis as a major means of molecular transformation refers to a technology of introducing a specific base pair at a designated site of a target DNA fragment to change an amino acid sequence encoded by the Site-directed mutagenesis is more rapid, direct and cost-effective than other strategies for improving a molecular structure, so it is one of the most commonly used genetic modification means in laboratories.

SUMMARY

The object of the invention is to improve the enzymatic activity and the temperature stability of modified arginine deiminase by means of molecular modification on arginine deiminase and to use the modified arginine deiminase for citrulline production and medicine.

The invention provides an arginine deiminase mutant with site-directed mutation modification. The arginine deiminase mutant is obtained by applying a site-directed mutagenesis technique based on an arginine deiminase gene of *Enterococcus faecalis* SK32.001. An amino acid sequence of the arginine deiminase mutant is SEQ ID NO:1, and the arginine deiminase mutant is encoded by an nucleotide sequence of SEQ ID NO:2.

The amino acid mutation happens outside an arginine deiminase protein structure, and the mutation may increase the protein hydrophobic interaction or electrostatic interaction.

Technical solutions of the invention: an arginine deiminase mutant with improved enzyme activity and temperature stability, of which an amino acid sequence is SEQ ID NO:1, is provided.

A nucleotide sequence of gene DNA of the arginine deiminase mutant with improved enzyme activity and temperature stability is shown as SEQ ID NO:2.

A recombinant plasmid comprises a DNA molecule.

A host cell comprises the DNA molecule or comprises the recombinant plasmid.

According to the arginine deiminase mutant with improved enzyme activity and temperature stability, an arginine deiminase mutant Gly292Pro with improved enzyme activity and temperature stability was obtained by transferring the recombinant plasmid comprising gene sequence DNA of an arginine deaminase mutant into an *Escherichia coli* BL21(DE3) host, constructing a mutant, and performing sequence verification and confirmation. Glycine Gly at position 292 is mutated into proline Pro.

A construction method of the arginine deiminase mutant with improved enzyme activity and temperature stability comprises the following steps:

1. designing a primer according to a gene sequence of arginine deiminase arcA of *Enterococcus faecalis* SK32.001; by taking *Enterococcus faecalis* SK32.001 comprising an arginine deiminase sequence as a template, obtaining a gene segment comprising arginine deiminase arcA by a PCR method to construct a recombinant plasmid with the connection to an expression vector pET-28a;

2. using B-FITTER software to recognize key amino acid residues that have adverse effects on temperature stability in enzyme molecules; then using SWISS-MODEL software to perform protein structure simulation on parent arginine deaminase, so as to obtain a tertiary structure of arginine deaminase; through comparative analysis, determining an amino acid site to be mutated is glycine at position 292;

3. designing a mutation primer, using a one-step PCR method to perform site-directed mutation on a nucleotide sequence of arginine deaminase, and replacing the amino acid at position 292 to obtain a recombinant vector comprising an arginine deaminase mutant gene sequence; and 4. enabling the recombinant vector comprising the arginine deaminase mutant gene sequence to enter competent cells of *Escherichia coli E. coli* BL21(DE3), inducing expression, collecting thalli, and using Ni-NTA for protein separation and purification after ultrasonication on cells to obtain an arginine deaminase mutant.

Application of the arginine deaminase mutant with improved enzyme activity and temperature stability: the arginine deaminase mutant is used for citrulline production and medication.

Beneficial effects of the invention: the arginine deaminase mutant provided by the invention has improved enzyme activity and temperature stability, wherein the enzyme activity is increased by 1.5 times and the half-life period at 40° C. is increased by 5.43 times. The invention optimizes and improves relieves wild type arginine deaminase, solves the problems of low enzyme activity and low temperature stability, and creates favorable conditions for the use of the enzyme in citrulline production and medication.

The arginine deaminase gene arcA used in the invention is derived from a strain of Enterococcus faecalis that can produce citrulline, CCTCC NO: M 2011465, which is deposited at the China Center for Type Culture Collection in Wuhan University, Wuhan, China, and is named as SK32.001 (Enterococcus faecalis SK32.001), and has been published in Chinese patent CN102433290A.

DETAILED DESCRIPTION

Figure 1:
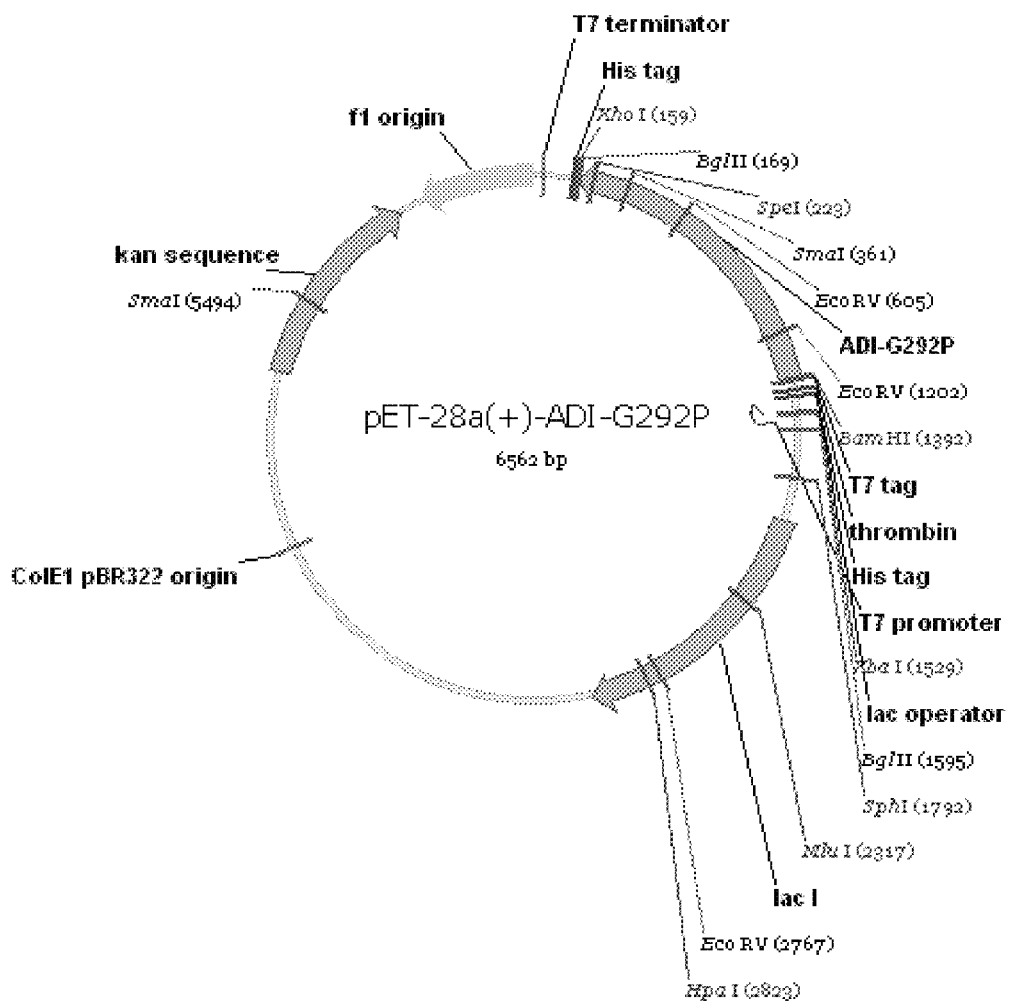
FIG. 1: Construction map of recombinant plasmid pET-28a-ADIG292P

The invention is further illustrated below by examples, which are for the purpose of illustration and are not intended to limit the scope of the invention.

Materials and reagents: restriction enzyme, Solution I ligase, PCR reagents and the like used herein were all purchased from TaKaRa Bio Inc.; plasmid extraction kit, genome extraction kit, agarose purification kit, Escherichia coli DH5a, BL21 (DE3) strains and primers were all purchased from Sangon Bioengineering (Shanghai) Co., Ltd.; other reagents were all analytical pure reagents purchased at home or abroad.

Example 1: Construction of Recombinant Plasmid

Enterococcus faecalis SK32.001 was cultured to an exponential growth metaphase, and 2 mL of a bacteria solution was centrifuged at 10000 r/min for 10 min. Supernatant was discarded, and lysozyme treatment was performed for 30 min. Genomic DNA was extracted according to kit instructions.

The following primers were designed for the amplification of arcA:

```
FADI-2:
5'-CGCGGATCCA TGAGTCATCC AATTAATGT-3'

(containing BamH I restriction enzyme cutting sites),
```

```
RADI-2:
5'-CCGCTCGAGT TAAAGATCTT CACGGT-3'

(containing Xho I restriction enzyme cutting sites).
```

PCR amplification conditions: 3 min of denaturation at 95° C., 30 cycles (95° C. 30 s, 55° C. 30 s, 72° C. 210 s), at last 2 min of extension at 72° C.

After purification on an amplification product, a PCR product and a vector pET-28a-c (+) were double-digested with BamH I and Xho I, and the digested products were respectively recovered and joint with Solution I ligase for 2 h at 16° C. for heat shock transformation into DH5a cells. When transformants grew on a plate, single colonies were picked into a liquid medium, and the plasmid was extracted. A recombinant plasmid pET-28a-ADI was verified through enzyme digestion. The recombinant plasmid was transformed into BL21 (DE3) cells to obtain BL21 (DE3)/pET-28a-ADI engineered bacteria.

Example 2: Determination of Arginine Deiminase Mutation Sites

Software B-FITTER was used to calculate a temperature factor (B-factor) of parent arginine deiminase amino acid residues to obtain amino acid residues with the highest temperature factor in an enzyme molecule; SWISS-MODEL software was used to simulate an arginine deiminase protein structure to obtain a tertiary structure model of arginine deiminase; Discovery Studio software was used for analyzing a spatial structure of and distance between the amino acid residues with the highest temperature factor and an enzyme catalytic activity center; and an amino acid site to be mutated was then determined to be glycine at position 292.

Example 3: Site-Directed Mutation

The primer design was performed based on a coding gene encoding arcA in Enterococcus faecalis SK23.001.

```
G292P-forward primer:
5'-CATCCAGAAA TCGAACCTGG CTTGGTTGTTT T-3',
and

G292P-reverse primer:
5'-TTCGATTTCT GGATGAATCG TAAATTTATC ATA-3',
``` wherein an underlined part represents a codon corresponding to glycine at position 292, encoded by a mutant gene.

PCR Amplification System:

| | |
|---|---|
| 10 × Reaction Buffer | 5 μL |
| dNTP mix | 1 μL |
| Forward primer (100 ng/μL) | 1.25 μL |
| Reverse primer (100 ng/μL) | 1.25 μL |
| Template pET-28a-ADI (10 ng) | 2 μL |
| pfuTurbo DNA polymerase (2.5 U/μL) | 1 μL |
| ddH$_2$O | 38.5 μL |

After PCR amplification, 1 μL of Dpn I restriction enzyme (10 U/μL) was added into the reaction solution and was thermally insulated at 37° C. for 1 hour to eliminate a template. A PCR product was transferred into Escherichia coli DH5α cells to coat the plate. Single colonies were picked to a liquid medium. A plasmid was extracted, and the correct mutant plasmid was obtained by sequencing. The successfully constructed mutant plasmid was transferred into *Escherichia coli* BL21 (DE3) to obtain a mutant strain BL21 (DE3)/pET-28a-ADIG292P.

Example 4: Expression and Purification of Wild Enzyme and Mutant Enzyme

Single colonies of BL21 (DE3)/pET-28a-ADI and BL21 (DE3)/pET-28a-ADIG292P were picked and put in an LB culture medium containing 0.5 mmol/L kanamycin, were cultured at 37° C. for 12 h at 200 r/min, then were transferred to an LB culture medium containing 0.5 mmol/L kanamycin, were cultured at 37° C. and 200 r/min until OD600 fell into the range of 0.5 to 0.7, and 1 mmol/L IPTG was added at the conditions of 28° C. and 200 r/min for 9h's induction.

After fermentation broth was centrifuged at 10000 r/min and 4° C. for 10 min, supernatant was discarded. Then the fermentation broth was washed twice with a phosphate buffer, a 15-20 mL phosphate buffer was added to suspend thalli, and ultrasonication was performed for 15 min (power of 22 W, 2 s of intermittence for each 1 s of ultrasonication). Centrifugation was performed at the conditions of 4° C. and 10000 r/min for 10 min, and supernatant was collected as crude enzyme solution and was filtered through a hydrophilic membrane with the pore diameter of 0.22 μm.

A Binding Buffer was used to pre-balance Ni2+chelating agarose resin column; the crude enzyme solution was added, and then the Binding Buffer and Washing Buffer were used for balancing separately; an Elution Buffer was used to elute the enzyme, and the enzyme was recovered; and the recovered enzyme solution was dialyzed in a dialysis buffer and then was restored in a 4° C. refrigerator.

Buffer preparations involved:
Phosphate Buffer (PB): 50 mmol/L, pH 5.5;
Binding Buffer: 50 mmol/L PB, 500 mmol/L NaCl, pH 7.0;
Washing Buffer: 50 mmol/L PB, 500 mmol/L NaCl, pH 7.0, 50 mmol/L imidazole;
Elution Buffer: 50 mmol/L PB, 500 mmol/L NaCl, pH 7.0, 500 mmol/L imidazole; and
the dialysis buffer: 50 mmol/L PB, pH 5.5, 10 mmol/L EDTA.

Example 5: Determination of Enzyme Activity and Temperature Stability of Wild Enzyme and Mutant Enzyme Definition of enzyme activity: Under this condition, the amount of enzyme for the catalytic production of 1 μmol of citrulline per minute is defined as one enzyme activity unit (U).

Figure 2:
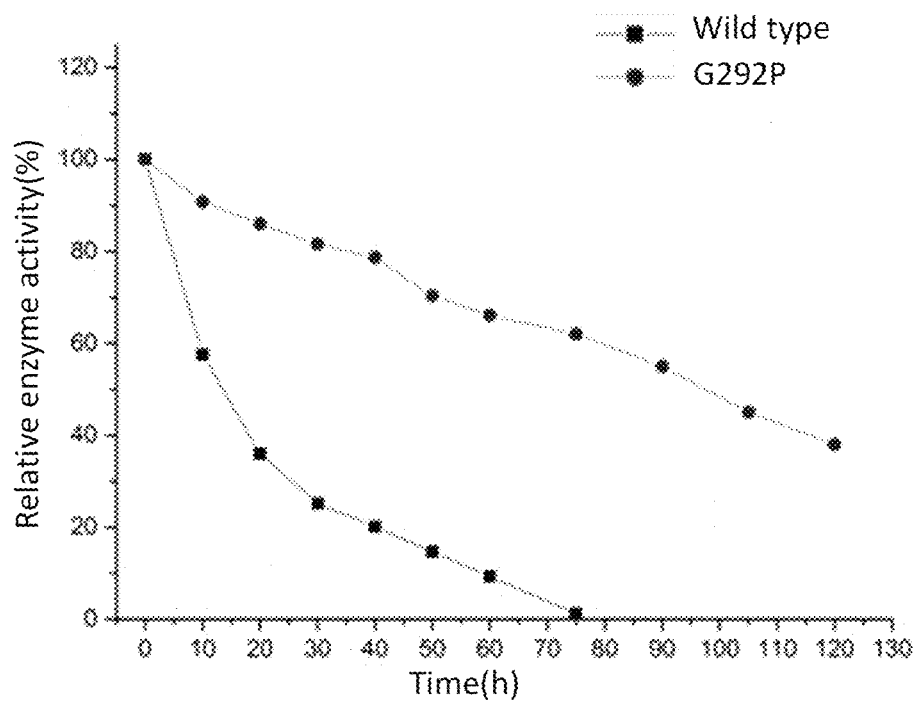
FIG. 2: Temperature stability of wild enzyme and mutant enzyme at 40° C.

Temperature stability: an enzyme solution was thermally insulated at 40° C., the time-gradient samples were taken out according to a time gradient, was added into a substrate L-arginine, and was placed in 45° C. water for a water bath for 10 min, and reaction was immediately terminated by boiling. Then citrulline yield was measured by HPLC, and relative enzyme activity was calculated. The enzyme activity of the untreated enzyme solution was defined as 100%, and the percentage of relative enzyme activity versus time was plotted to assess the temperature stability of enzyme. Results obtained are shown in FIG. 2: half-life period of the enzyme of a mutant G292P was prolonged to 91.8 min from 16.9 min of the wild enzyme, and was increased by 5.43 times.

Example 6: Efficient Synthesis of Citrulline

Figure 3:
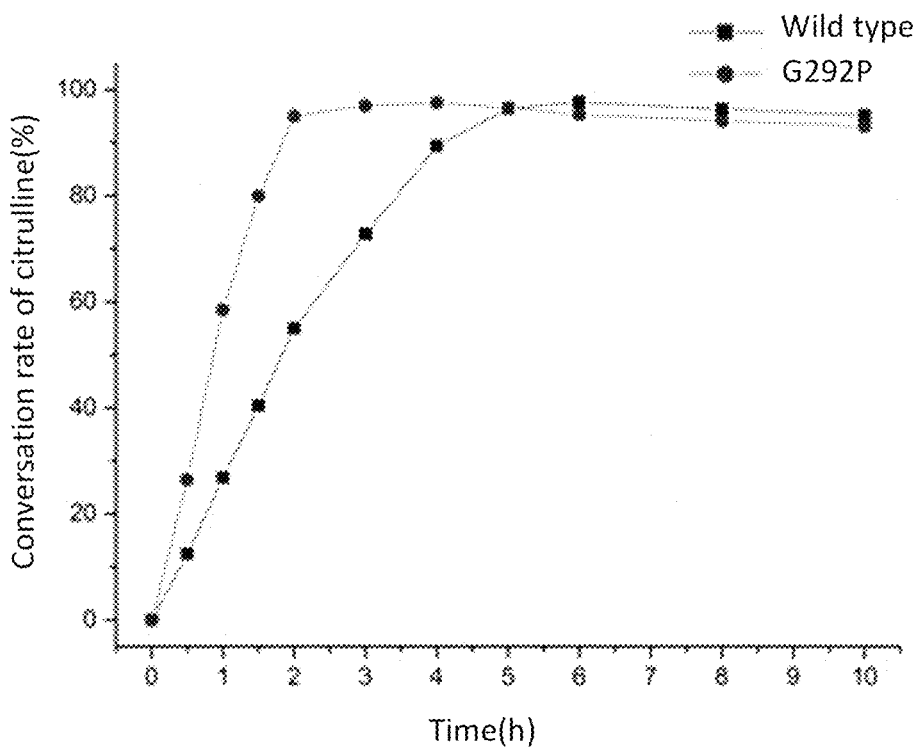
FIG. 3: Conversion rate of biosynthesized citrulline of wild enzyme and mutant enzyme

Separately take 1 g of bacteriophage of wild enzyme and mutant enzyme into 50 mL L-arginine solution with a concentration of 100 g/L. Reaction was carried out at 45, 150 r/min and pH 6.0-6.5, and timing sampling and citrulline yield analysis were performed. Results are shown in FIG. 3: 95% or more of arginine was converted into citrulline by wet thalli of the mutant enzyme after 2 h., and 95% or more of arginine was converted into citrulline by wet thalli of the wild enzyme after 5 h.

The citrulline yield in this example was 95% or more.

Through the invention, a higher concentration of citrulline can be obtained by enzymatic conversion in a relatively short period of time, which lays a foundation for future industrial application.

What is claimed is:

1. An arginine deiminase mutant, comprising the amino acid sequence set forth in SEQ ID NO: 1, wherein the mutant comprises mutation Gly292Pro compared to a parent arginine deiminase, greater enzyme activity and greater temperature stability than the parent arginine deiminase.

2. The arginine deiminase mutant of claim 1, wherein the mutant is engineered starting with arginine deiminase sequences obtained from bacteria, archaebacteria, or eukaryotic cells.

3. The arginine deiminase mutant of claim 2, wherein the bacteria is obtained from *Enterococcus faecalis* SK32.001.

4. The arginine deiminase mutant of claim 1, wherein the mutant is encoded by SEQ ID NO:2.

5. The arginine deiminase mutant of claim 1, wherein temperature stability of the mutant is increased at least 5-fold at 45° C. compared to the parent arginine deiminase.

6. The arginine deiminase mutant of claim 1, wherein the enzyme activity is increased at least 2.5-fold higher than the parent arginine deiminase.

* * * * *